United States Patent [19]
Niino et al.

[11] Patent Number: 4,744,649
[45] Date of Patent: May 17, 1988

[54] OPHTHALMOLOGICAL MEASURING APPARATUS

[75] Inventors: Masao Niino, Okazaki; Nobuyuki Yasuda, Gamagori; Koichiro Kakizawa, Okazaki; Tadashi Ichihashi; Masunori Kawamura, both of Hino, all of Japan

[73] Assignee: Kowa Kabushiki Kaisha, Nagoya, Japan

[21] Appl. No.: 863,046

[22] Filed: May 14, 1986

[30] Foreign Application Priority Data

May 15, 1985 [JP] Japan ................. 60-103177

[51] Int. Cl.$^4$ ........................ A61B 3/10; A61B 3/14
[52] U.S. Cl. ................. 351/221; 351/205; 351/211; 351/214
[58] Field of Search ........... 351/205, 211, 214, 221; 354/206, 62

[56] References Cited

U.S. PATENT DOCUMENTS 3,850,527 11/1974 Withrop et al. ............ 351/205
4,523,821  6/1985 Lang et al. ................ 351/214
4,679,917  7/1987 Genco et al. .............. 351/221

Primary Examiner—Rodney B. Bovernick
Assistant Examiner—Jay P. Ryan
Attorney, Agent, or Firm—Dennison, Meserole, Pollack & Scheiner

[57] ABSTRACT

An ophthalmological measuring apparatus having a laser-slit projector unit for projecting a laser beam on a portion in a human eyeball, a microscope unit adapted for receiving and observing the light reflected from the portion in the eyeball and a detector unit adapted for displaying the observing point in the eyeball projected by the laser beam. The microscope unit includes an objective optical system, an imaging optical system, a scattered light pickup prism disposed between the objective optical system and the imaging optical system and having a reflecting surface for diverging and directing a part of the reflected light, a beam splitter for superposing another optical axis parallel to the optical axis diverged by the prism on the optical axis of the imaging optical system, a converging optical system for receiving the diverged optical axis and the other optical axis parallel thereto, and an optical fiber having one end disposed adjacent to the focal plane of the converging optical system and movable up and down and right and left. The detector unit includes a photoelectric device directed to the other end of the optical fiber, a wavelength separating mirror disposed between the other end of the optical fiber and the photoelectric device, a light emitting diode disposed on the reflecting side of the mirror and adapted for emitting light having a wavelength different from that of the laser beam, and a right-to-left inverting optical system disposed between the beam splitter and the converging optical system.

5 Claims, 3 Drawing Sheets

OPHTHALMOLOGICAL MEASURING APPARATUS

BACKGROUND OF THE INVENTION

1. Field of the Invention

The present invention relates to an ophthalmological measuring apparatus, and more specifically to such an ophthalmological measuring apparatus using a laser beam.

2. Description of the Prior Art

A cataract, which is one of ophthalmological diseases, is a condition in which protein particles of the crystalline lens become large in size and the crystalline lens becomes opaque, and in order to discover the cataract early for proper remedy or precautionary treatment, it is necessary to measure the size or diameter of the protein particles.

A human eyeball includes various transparent bodies, such as cornea, crystalline lens and vitreous body, in which minute protein particles are floating in Brownian movement. In a normal eye the protein particles of small diameters are widely distributed, while in case of an opaque eye the protein particles of diameters larger than those in case of the normal eye are widely distributed.

In order to measure the diameter, the following method has been proposed heretofore and is now in use.

The method includes the steps of converging a laser beam on a point within the crystalline lens, detecting the intensity of scattered light scattered by protein particles being in Brownian movement when they pass across the point, obtaining by a correlator the correlation function as to the fluctuation of the scattered light intensity as the time elapses, calculating from the obtained result relaxation time of the fluctuation of the scattered light intensity, and obtaining the diffusion coefficient of the protein particles from the calculated time, thereby obtaining the diameter of the protein particles.

Such a method is carried out by a conventional apparatus as is shown in FIG. 4. As may be seen, the conventional apparatus includes a projector unit 101 for projecting a laser beam, a slit image and a spot image on a portion in the eye E to be examined, a microscope unit 102 having a beam splitter 103 for receiving the light reflected at the portion of the eye E and separating the same in two directions and incorporating a photomultiplier tube 104, a time correlator 105 connected to the photomultiplier tube 104 and an analyzer 106 connected to the time correlator 105. In order to take measurement, the projector unit 101 and the microscope unit 102 are disposed in front of the eye E to be examined.

When a measurement is taken, at first a lamp 107 is turned on, and the light emitted therefrom is converged by a lens 108 on a slit portion of a slit 109 and, after passing therethrough, it is reflected by a mirror 110, passes through a half mirror 111 and goes into a lens 112, reflected by a moving mirror 113 and goes along the optical axis $X_1$ to form a slit image on a portion in the eye E including a measuring point P by a projecting lens 114.

When a lamp 115 is turned on, the light therefrom illuminates a pin hole 116 and forms a spot image or pin hole image on the measuring point P through the lens 112, the moving mirror 113 and the projecting lens 114 which are optically in conjugate relation to each other.

While the slit image or the spot image is observed through an eyepiece 117 on an observing system optical axis $X_3$ extending at a predetermined angle to the optical axis $X_1$, the projecting angle to the eye E to be examined, that is the optical axis $X_1$, and the optimum observing angle to the optical axis $X_1$, that is the orientation of the optical axis $X_3$ in relation thereto are adjusted so that observation and measurement at the measuring point P can be made in the optimum condition.

Then, the moving mirror 113 is moved in the direction of an arrow A to be retracted from the optical path of the optical axis $X_1$, and a laser tube (not shown) is actuated to emit a laser beam L.

The laser beam L, once converged by a condenser lens 118, is diverged and goes into a collimating lens 119 in which the laser beam L becomes substantially parallel. The parallel beam reaches the projecting lens 114 by which it is converged and directed to the measuring point P.

The laser beam scattered at the the measurement point P partly goes through the beam splitter 103 and then through an objective lens 120 and an imaging lens 121 to be observed by the eyepiece 117. At the same time, a part of the laser beam scattered is reflected by the reflecting surface 103a of the beam splitter 103 and directed to the photomultiplier tube 104 to be measured by a measuring device connected thereto.

Thus, in the above mentioned conventional apparatus in which the slit illuminating system and the spot illuminating system are superposed on the optical path of the laser beam for measurement, preliminary observation and adjustment of the measuring location may be easily made and its operation may be quickly accomplished. However, as the optical axis in which the laser beam is projected and the optical axis of the microscope are arranged at a certain angle to each other, they are refracted differently on the surface of the eyeball, causing a slight locational difference between the convergent point of the laser beam and the focal point of the microscope. Therefore, at some depths in the eyeball the convergent point of the laser beam does not conform to the location at which the scattered light is measured. Furthermore, the conventional apparatus is disadvantageous in that the area of measurement cannot be assured.

SUMMARY OF THE INVENTION

It is an object of the present invention to eliminate the above disadvantages associated with the prior art by providing an ophthalmological measuring apparatus which facilitates reproducibility of observation and measurement, which permits minute adjustment of the observing point, and which provides ease of assuring of the measuring area.

The ophthalmological measuring apparatus according to the present invention comprises a laser-slit projector unit for projecting a laser beam on a portion in a human eyeball, a microscope unit adapted for receiving and observing the light reflected from the portion in the eyeball and a detector unit for displaying the observing point in the eyeball projected by the laser beam. The microscope unit includes an objective optical system, an imaging optical system, a scattered light pickup prism disposed between the objective optical system and the imaging optical system and having a reflecting surface for diverting and directing a part of the reflected light, a beam splitter for superposing another optical axis parallel to the optical axis diverged by the prism on the optical axis of the imaging optical system, a converging optical system for receiving the diverged optical axis and the other optical axis parallel thereto, and an optical fiber having one end disposed adjacent to the focal plane of the converging optical system and movable up and down and right and left. The detector unit includes a photoelectric device directed to the other end of the optical fiber, a wavelength separating mirror disposed between the other end of the optical fiber and the photoelectric device, a light emitting diode disposed on the reflecting side of the mirror and adapted for emitting light having a wavelength different from that of the laser beam, and a right-to-left inverting optical system disposed between the beam splitter and the converging optical system.

The invention will become more fully apparent from the claims and the description as it proceeds in connection with the drawings.

DETAILED DESCRIPTION OF A PREFERRED EMBODIMENT

Figure 1:
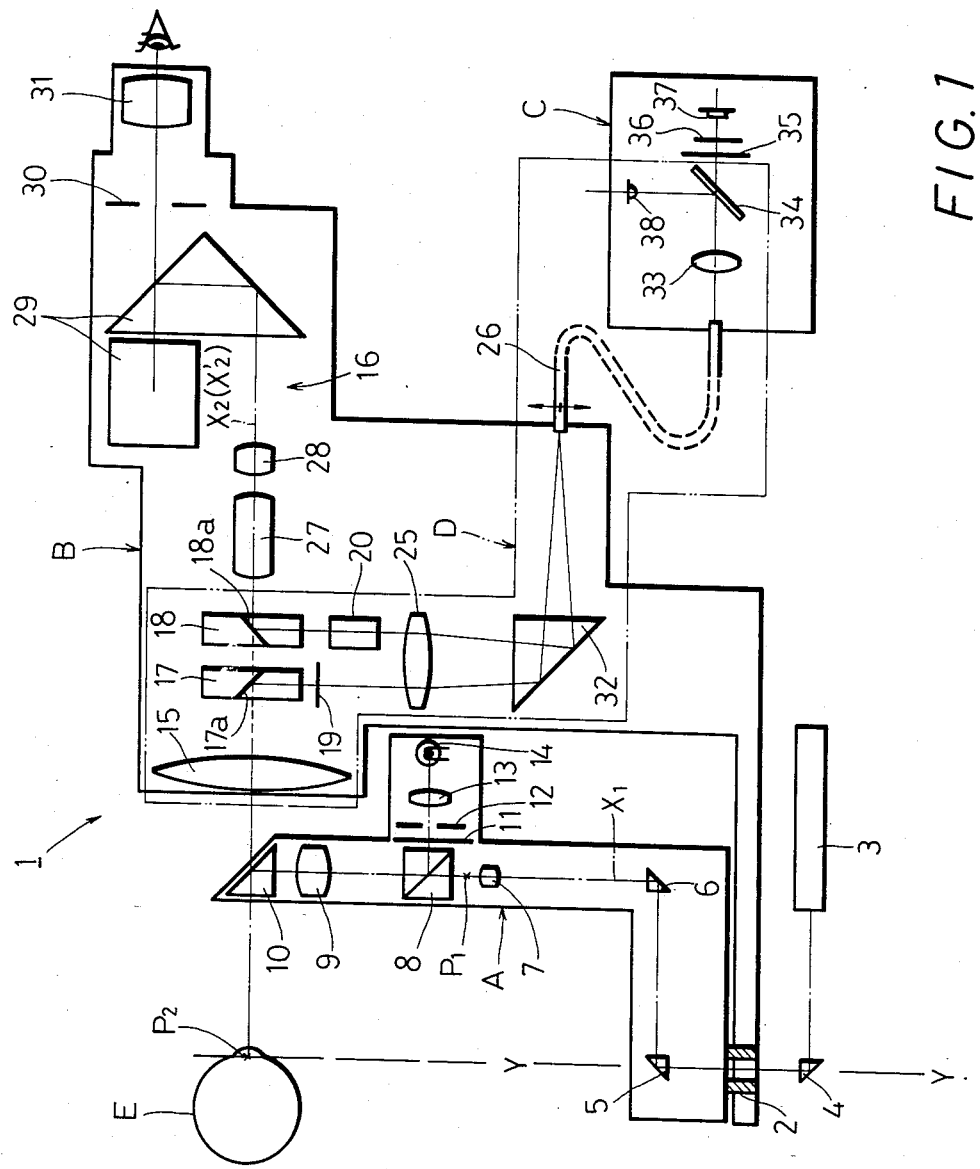
FIG. 1 is a diagrammatic view of an embodiment of the present invention illustrating the vertical optical paths and the arrangement of various components.

Referring now to FIG. 1, shown therein and generally designated by the reference numeral 1 is an ophthalmological measuring apparatus constructed in accordance with the invention. As shown therein, the apparatus 1 is composed of a laser-slit projector unit A, a microscope-detector optical system unit B and a detector unit C.

The laser-slit projector unit A is pivotally movable within a predetermined range of angles around a cylindrical shaft 2 in relation to the microscope-detector optical system unit B in such a manner as to prevent relative interference. A He.Ne laser tube 3 emits a laser beam which is directed by a directing prism 4 disposed on the axis Y of the cylindrical shaft 2 so as to travel upwardly along the axis Y, and then it is reflected by the directing prisms 5 and 6, so that the optical axis $X_1$ of the laser beam is directed upwardly. The laser-slit projector unit A also includes a laser beam converging optical system 7, a beam splitter 8, a projecting optical system 9 and a projecting prism 10 arranged in series on the optical axis $X_1$. The laser beam is converged on a point $P_1$ on the optical axis $X_1$ by the laser beam converging optical system 7, passes through the beam splitter 8 and is again converged by the projecting optical unit 9 and directed horizontally by the projecting prism 10 so as to be converged on a point $P_2$ in the extension of the axis Y of the cylindrical shaft 2. The point $P_2$ is to be located in the crystalline lens of an eye E to be examined. Furthermore, at the back of the beam splitter 8, the laser-slit projector unit A has a shutter 11, a slit 12, a condenser optical system 13 and a lamp 14, so that the converged light is composed by the beam splitter 8 to form a slit image on the point $P_2$.

Figure 2:
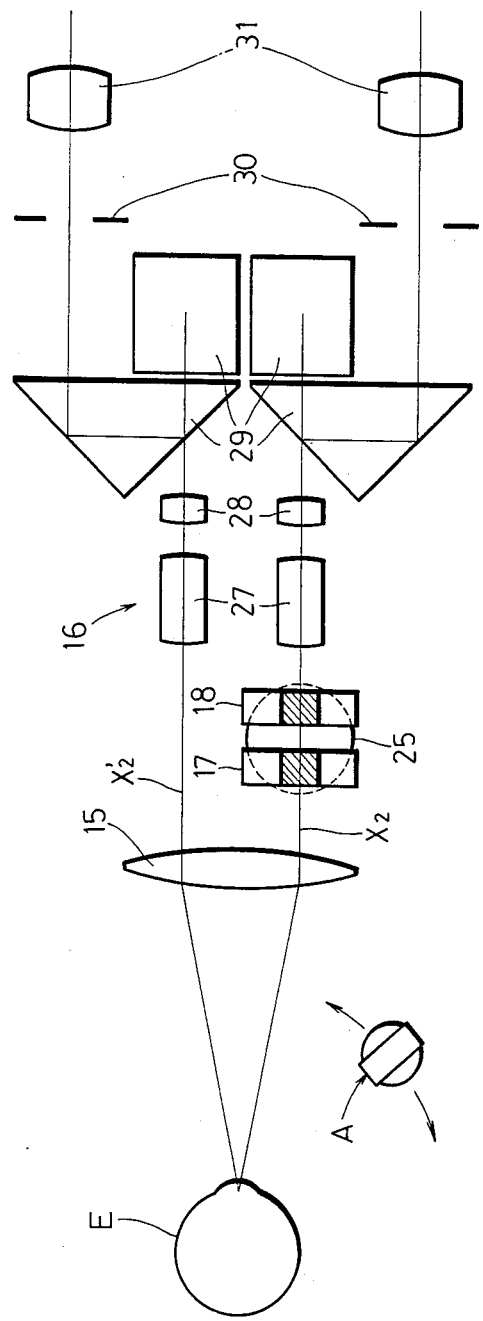
FIG. 2 is a diagrammatic view illustrating the horizontal optical paths and the arrangement of various components of the apparatus in FIG. 1.
Figure 3:
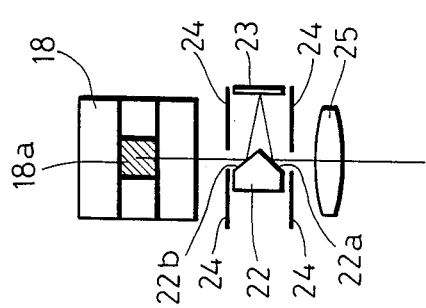
FIG. 3 is a diagrammatic view illustrating a right-to-left inverting optical system of the apparatus in FIG. 1.
Figure 4:
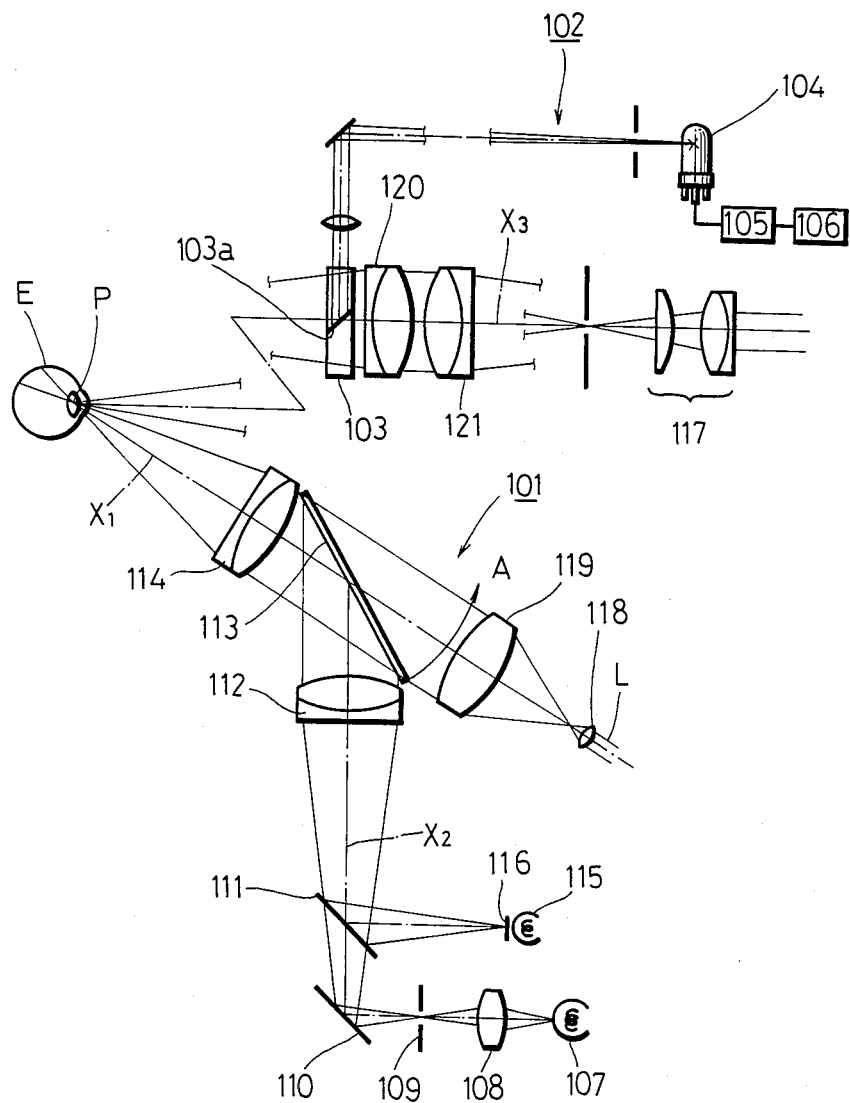
FIG. 4 is a diagrammatic view illustrating the optical paths and the arrangement of a prior art apparatus.

The microscope-detector optical system unit B is disposed at the back of the laser-slit projector unit A, and has in the front portion thereof an objective optical system 15 slidingly movable front and back, its front focus conforming to the point $P_2$. Disposed at the back of the objective optical system 15 is a binocular optical system 16, which may be called a binocular microscope, composed of a pair of optical systems (FIG. 2), in which a scattered light pickup prism 17 is disposed on the optical axis $X_2$ immediately behind the objective optical system 15 and has a reflecting surface 17a for reflecting downwardly a part of the incident light from the objective optical system 15. Disposed immediately behind the pickup prism 17 is a beam splitter 18 having a reflecting surface 18a for reflecting backwardly the incident light from the downwardly directed portion of the beam. Provided just under the scattered light pickup prism 17 is a wavelength separating filter 19 such as R-60 which transmits the light having a wavelength of about 633 nm but cuts off the light having a wavelength of about 560 nm so as to prevent incidence of the light having a wavelength of 560 nm from a later described optical fiber 26 into the eye to be examined. A right-to-left inverting optical system 20 is disposed directly under the beam splitter 18. As shown in FIG. 3, the right-to-left inverting optical system 20 is composed of a prism 22 having two gable-shaped reflecting surfaces 22a and 22b, a flat mirror 23 disposed in opposition to the prism 22 and flags 24 for eliminating the light which would pass without being reflected by these three reflecting surfaces. A converging optical system 25 is disposed under the wavelength separating filter 19 and the right-to-left inverting optical system 20 and has a focal plane on which the front end of an optical fiber 26 is disposed movably up and down and right and left. As best shown in FIG. 2, the binocular optical system or binocular microscope 16 further has, on the optical axes $X_2$ and $X'_2$ behind the beam splitter 18, magnification changers 27, imaging optical systems 28, erecting optical systems 29, reticles 30 and ocular optical systems 31, respectively arranged in pairs. Numeral 32 indicates a directing prism.

The detector unit C is connected through the optical fiber 26 to the microscope-detector optical system unit B and includes a condenser optical system 33 disposed behind the rear end of the optical fiber 26 and a wavelength separating mirror 34 disposed behind the condenser optical system 33. At an incident angle of 45 degrees the wavelength separating mirror 34 transmits the light having a wavelength of 633 nm and the light having a wavelength of about 560 nm. A wavelength separating filter 35, a shutter 36 and a photoelectric device 37 are disposed on the transmitting side of the wavelength separating mirror 34, and a light emitting diode 38 for emitting the light having a wavelength of 560 nm is provided on the reflecting side thereof. The shutter 36 is released at measurement. The light given to the photoelectric device 37 is converted into an electric output, which is transmitted to a correlator (not shown) and calculated to obtain the average diameter of the particles and others.

In the ophthalmological measuring apparatus 1 thus constructed, a measuring location assuring mechanism D is formed which includes the objective optical system 15, scattered light pickup prism 17, wavelength separating filter 19, converging optical system 25, directing prism 32, optical fiber 26, condenser optical system 33, wavelength separating mirror 34, light emitting diode 38, right-to-left inverting optical system 20 and beam splitter 18.

The overall operation is as follows. When a measurement is taken, the laser tube 3 emits a laser beam having a wavelength of 633 nm, which passes through the directing prisms 4, 5 and 6 and is once converged on the point $P_1$ by the laser beam converging optical system 7 and then diverged, passes through the beam splitter 8 and is again converged by the projecting optical system 9 and then reflected horizontally by the projecting prism 10 to be converged on the point $P_2$. In the apparatus of the preferred embodiment, the light once converged on the point $P_1$ is again converged on the point $P_2$. In general, the laser beam emitted from a laser tube has a small diameter between 0.5 to 1.0 mm and if the beam is to be directly converged to obtain a small beam diameter of about 20 μm, a lens having numerical aperture of more than 0.02 is required, and in that case, the focal length of the lens becomes less than 25 mm, which is unfavorable because a long working distance becomes difficult to obtain. Furthermore, in order to prevent any damage to the retina, a larger numerical aperture is preferable. Then, in this embodiment, the converging optical system 7 having a small focal length is first used to assure a required numerical aperture and the projecting optical system having a long focal length is used to obtain a small beam diameter with a long working distance assured. In the process mentioned above, the laser beam of a very high energy density may be obtained at the point $P_2$.

When the lamp 14 is turned on, the light emitted therefrom is converged by the condenser optical system 13 on the slit portion of the slit 12, and after passing therethrough, it is composed into a slit projection by the beam splitter 8 and thus a slit image is formed on the point $P_2$.

The light reflected at the point $P_2$ into scattered light partly goes to the objective optical system 15. A part of the incident light passes through the scattered light pickup prism 17 and the beam splitter 18 to be observed by the binocular optical system 16. On the other hand, the light reflected by the reflecting 17a of the scattered light pickup prism 17 passes through the wavelength separating filter 19 and is converged through the directing prism 32 on the front end of the optical fiber 26 by the converging optical system 25. The light then passes through the optical fiber 26 up to the wavelength separating mirror 34. The wavelength separating mirror 34, which, at an incident angle of 45 degrees, transmits the light having a wavelength of about 633 nm and reflects the light having a wavelength of about 560 nm, transmits the above light, which then goes to the photoelectric device 37. At measurement and observation, the light emitting diode 38 is turned on, and green light therefrom, which has a wavelength of 560 nm, is reflected by the wavelength separating mirror 34 and converged on the rear end of the optical fiber 26 by the condenser optical system 33, and then it goes through the optical fiber 26 and is directed upwardly by the directing prism 32 up to the right-to-left inverting optical system 20. The light is then reflected by the reflecting surface 18a of the beam splitter 18 and goes through the magnification changers 27, imaging optical systems 28 and erecting optical systems 29, so that a green spot image is indicated in the observation field of the binocular optical system 16. As the spot image, the front end of the optical fiber 26 and the point in the eyeball corresponding to the location of the spot image in the observation field are in optically conjugate relation to each other and the point indicated by the spot image designates the measuring location at the point $P_2$, the spot image can be easily superposed on the location on which the laser beam is projected by moving the front end of the optical fiber 26 up and down and right and left. The scattered light reflected at the location goes through the objective optical system 15, scattered light pickup prism 17, wavelength separating filter 19, converging optical system 25, directing prism 32, optical fiber 26, condenser optical system 33 and wavelength separating mirror 34 to the photoelectric device 37, in which the light is converted into an electric output to be transmitted to the correlator and calculated to obtain the average diameter of the particles.

In this way, the green spot image of the light emitting diode 38 can be easily superposed on the location on which the laser beam is projected by moving the front end of the optical fiber 26 up and down and right and left, so that the measuring location can be assured and, for example, when the angular location of the laser-slit projector unit A is varied to displace the location on which the laser beam is projected to a desired position, measurement can be easily carried out at the position by superposing the spot image thereon. Also, in addition to the laser beam and the slit image, the green spot image is provided and is movable up and down and right and left so that it may be composed into the varying observation image at the point $P_2$ and therefore, reproducibility of the observation and measurement may be greatly facilitated. Furthermore, the size of the spot image indicates the area of measurement, permitting easy grasping of the area of measurement in addition to the location thereof. The sliding movement of the objective optical system 15 permits adjustment of the front-to-back displacement and therefore, a sharp observation image can be obtained.

Though, in the above embodiment, the magnification changers 27 are disposed at the back of the beam splitter 18, such an arrangement is not limitative, and omission of the magnification changers 27 do not degrade the effect of the apparatus of the embodiment. However, such an arrangement of the magnification changers 27 at the back of the beam splitter 18 as shown in the drawing permits change of the observing magnification at the measuring location without changing the measuring area. On the contrary, when the magnification changers 27 are disposed in front of the scattered light pickup prism 17, change of the observing magnification results in corresponding change of the extent of the measuring area. Furthermore, sliding movement of the objective optical system 15 permits adjustment of the front-to-back displacement. Though the front-to-back displacement is small in comparison with the right-to-left displacement, the observation image tends to be out of focus when the observation is made at a high magnification by the magnification changers 27. Thus, the adjustment of the objective optical system 15 is remarkably effective to obtain a sharp observation image.

These and other modifications to the preferred embodiment of the invention as described herein can be made without departing from the spirit or scope thereof as defined by the appended claims.

What is claimed is:

1. An ophthalmological measuring apparatus comprising:
   a laser-slit projector means for projecting a laser beam on a point in a human eyeball;

a microscope means adapted for receiving and observing the light said reflected from the point in the human eyeball, and said microscope means including:
  objective optics (15);
  imaging optics (28);
  a scattered light pickup prism (171) disposed between said objective optics (15) and said imaging optics (28) and having a reflecting surface (17a) for diverting and directing a part of the reflected light;
  beam splitter means (18) for superposing another optical axis parallel to the optical axis diverged by said prism on the optical axis of said imaging optics (28);
  converging optics (25) for receiving the diverged optical axis and the other optical axis parallel thereto; and
  an optical fiber (26) having a first and a second end with the first end disposed adjacent to the focal plane of said converging optical system and said optical fiber (26) being movable up and down and right and left; and
detector means (c) adapted for displaying and observing the point in the eyeball projected by the laser beam and said detector means including
  a photoelectric device (37) in the optical path of the second end of said optical fiber;
  a wavelength separating mirror (34) disposed between the second end of said optical fiber and said photoelectric device; and
  a light emitting diode (38) disposed on the reflecting side of said mirror (34) and adapted for emitting light having a wavelength different from that of the laser beam; and
  right-to-left inverting optics (20) disposed between said beam plitter (18) and said converging optics (25).

2. The ophthalmological measuring apparatus as defined in claim 1, further comprising a wavelength separating filter (19) disposed between said scattered light pickup prism (17) and said converging optics (25) and adapted for transmitting the laser beam and cutting off the light from said light emitting diode.

3. The ophthalmological measuring apparatus as defined in claim 1, further comprising a pair of magnification changers (27) disposed between said beam splitter means (18) and said imaging optics (28).

4. The ophthalmological measuring apparatus as defined in claim 1, further comprising a pair of magnification changers (27) disposed between said objective optics (15) and said scattered light pickup prism (17).

5. The ophthalmological measuring apparatus as defined in claim 1 wherein said objective optics (15) are slidingly movable front and back along the optical axis thereof.

* * * * *